(12) United States Patent
Chen et al.

(10) Patent No.: US 6,562,994 B2
(45) Date of Patent: May 13, 2003

(54) PROCESS FOR THE PREPARATION OF N-(SUBSTITUTED PHENYL)-3-ALKYL-,ARYL- AND HETEROARYLSULFONYL-2-HYDROXY-2-ALKYL- AND HALOALKYLPROPANAMIDE COMPOUNDS

(75) Inventors: Bang-Chi Chen, Plainsboro, NJ (US); Joseph E. Sundeen, Yardley, PA (US); Rulin Zhao, Pennington, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/953,759

(22) Filed: Sep. 17, 2001

(65) Prior Publication Data

US 2002/0086902 A1 Jul. 4, 2002

Related U.S. Application Data

(60) Provisional application No. 60/234,121, filed on Sep. 21, 2000.

(51) Int. Cl.$^7$ .................. C07C 255/00; C07C 315/00; C07C 317/00
(52) U.S. Cl. ........................... 558/413; 560/11
(58) Field of Search ........................ 558/413

(56) References Cited

U.S. PATENT DOCUMENTS

| 4,636,505 A | 1/1987 | Tucker ...................... 514/256 |
| 4,835,312 A | 5/1989 | Itoh et al. | |

FOREIGN PATENT DOCUMENTS

| EP | 100 172 A1 | 2/1984 | ......... C07C/149/23 |
| GB | 0543631 A2 * | 11/1992 | |

OTHER PUBLICATIONS

Tucker et al, Nonsteroidal Antiandrogens. Synthesis and Structure–Activity Relationships of 3–Substituted Derivatives of 2–Hydroxypropionanilides, 1988, Journal of Medicinal Chemistry, 31, pp. 954–959).*

P. Schellhammer, Exp. Opin. Invest. Drugs, vol. 8, No. 6, pp. 849–860 (1999).
H. Tucker and G. Chesterson, J. Med. Chem., vol. 31, pp. 885–887 (1988).
J. Dalton, et al., Biochemical and Biophysical Research Communications, vol. 244, pp. 1–4 (1998).
D. McKillop, et al., Xenobiotica, vol. 25, No. 6, pp. 623–634 (1995).
A. Maucher, et al., J. Cancer Res. Clin. Oncol., vol. 119, pp. 669–674 (1993).
K. Goa, et al., Drugs & Aging, vol. 12, No. 5, pp. 401–422 (1998).
B. Furr, Eur. Urol., vol. 29, Suppl. 2, pp. 83–95 (1996).
B. Furr, et al., Urology, vol. 47, Suppl. 1A, pp. 13–25 (1996).
W. D. Emmons et al., "Peroxytrifluoroacetic Acid. IV. The Epoxidation of Olefins", J. Am. Chem. Soc., vol. 77, No. 1, pp. 89–92 (1955).
C. G. Venier, "Peroxytrifluoroacetic Acid. A Convenient Reagent for the Preparation of Sulfoxides Sulfones", J. Org. Chem., vol. 47, No. 19, (1982), pp. 3773–3774.

* cited by examiner

*Primary Examiner*—Johann Richter
*Assistant Examiner*—Paul A. Zucker
(74) *Attorney, Agent, or Firm*—Deanna L. Baxam

(57) ABSTRACT

The present invention provides an improved process for the preparation of N-(substituted phenyl)-3-alkyl-, aryl- and heteroarylsulfonyl-2-hydroxy-2-alkyl- and haloalkylpropanamide compounds of formula I that exhibit antiandrogenic activity and are useful in the treatment of malignant or benign prostatic disease or of androgen dependent disease conditions such as acne, hirsutism or seborrhea.

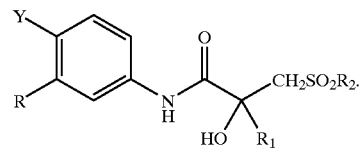

23 Claims, No Drawings

PROCESS FOR THE PREPARATION OF N-(SUBSTITUTED PHENYL)-3-ALKYL-, ARYL- AND HETEROARYLSULFONYL-2-HYDROXY-2-ALKYL- AND HALOALKYLPROPANAMIDE COMPOUNDS

RELATED APPLICATION

This application claims the benefit under Title 35§ 119(e) of U.S. Provisional Application No. 60/234,121, filed Sep. 21, 2000.

BACKGROUND OF THE INVENTION

U.S. Pat. No. 4,636,505 describes N-(substituted phenyl)-3-alkyl-, aryl- and heteroarylsulfonyl-2-hydroxy-2-alkyl- and haloalkylpropanamide compounds, methods for their preparation, and their utility in the treatment of malignant or benign prostatic disease or of androgen dependent disease conditions such as acne, hirsutism or seborrhoea. Bicalutamide, (±)-N-[4-cyano-3-(trifluoromethyl)phenyl]-3-[(4-fluorophenyl)sulfonyl]-2-hydroxy-2-methylpropanamide, is a particularly preferred specie of the above compounds. Bicalutamide is an effective, well-tolerated and convenient non-steroidal antiandrogen for use in the treatment of advanced prostate cancer. Preclinical and clinical studies have also indicated its potential as monotherapy, with quality of life advantages compared with castration (Schellhammer, Exp. Opin. Invest. Drugs, 8, p. 849 (1999)).

Bicalutamide has been prepared by reacting 3-trifluoromethyl-4-cyanoanaline with methacryloyl chloride followed by epoxidation of the resultant N-(3-trifluoromethyl-4-cyanophenyl)methacrylamide and subsequent epoxide ring opening with thiol and sulfone formation (U.S. Pat. No. 4,636,505; Tucker et al., J. Med. Chem., 31, p. 954 (1988)). Although that process is relatively straight forward, chromatographic separations required in the process makes it undesirable for use on a commercial scale. In addition, that process requires the use of relatively expensive starting materials.

Accordingly, what is needed in the art is a process for the preparation of N-(substituted phenyl)-3-alkyl-, aryl- and heteroarylsulfonyl-2-hydroxy-2-alkyl- and haloalkylpropanamide compounds which does not require the use of chromatographic separations and uses less expensive starting materials.

It is, therefore, an object of the present invention to provide an improved process for the preparation of N-(substituted phenyl)-3-alkyl-, aryl- and heteroarylsulfonyl-2-hydroxy-2-alkyl- and haloalkylpropanamide compounds which does not require the use of chromatographic separations and uses relatively less expensive starting materials compared to the art processes.

This and other objects and features of the present invention are described hereinbelow in more detail.

SUMMARY OF THE INVENTION

The present invention provides an improved process for the preparation of an N-(substituted phenyl)-3-alkyl-, aryl- or heteroarylsulfonyl-2-hydroxy-2-alkyl- or haloalkylpropanamide of formula I

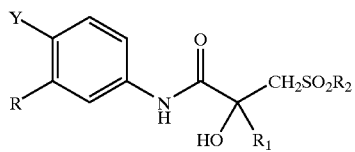

wherein
Y is cyano, nitro, perfluoroalkyl, alkylcarbonyl, alkoxycarbonyl or alkylsulfonyl;
R is perfluoroalkyl, cyano, nitro, alkylcarbonyl, alkoxycarbonyl, alkyl or alkoxy;
$R_1$ is alkyl or haloalkyl; and
$R_2$ is alkyl, aryl or heteroaryl,
which process comprises:

(a) reacting a substituted benzene of formula II (II)

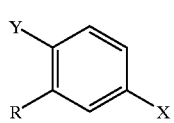

wherein Y and R are as described above, X is F, Cl, Br, I or $-OSO_2R_3$, and $R_3$ is alkyl or aryl with an α,β,-unsaturated propanamide of formula III

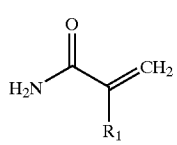

wherein $R_1$ is as described above in the presence of a first base to form an N-(substituted phenyl)-α,β-unsaturated propanamide of formula IV

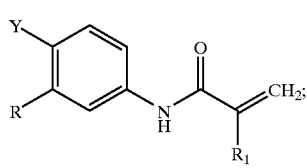

(b) reacting the formula IV propanamide with an epoxidizing agent to form an epoxide of formula V

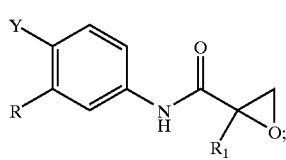

(c) reacting the formula V epoxide with a thiol of formula VI $R_2SH$     (VI)

wherein $R_2$ is as described above in the presence of a second base to form a sulfide of formula VII

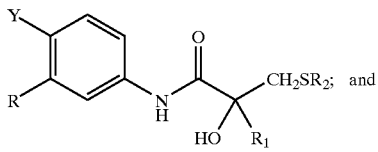

(VII)

(d) reacting the formula VII sulfide with an oxidizing agent.

The present invention also relates to improved processes for the preparation of N-(substituted phenyl)-α,β-unsaturated propanamides of formula IV, epoxides of formula V, and sulfides of formula VII.

DETAILED DESCRIPTION OF THE INVENTION

The process of the present invention preferably comprises reacting a substituted benzene of formula II with an α,β-unsaturated propanamide of formula III in the presence of a first base and an aprotic solvent, preferably in a temperature range from about −40° C. to 155° C., to form an N-(substituted phenyl)-α,β-unsaturated propanamide of formula IV; reacting the formula IV propanamide with an epoxidizing agent in the presence of an aprotic solvent, preferably in a temperature range from about −78° C. to 155° C., to form an epoxide of formula V; reacting the formula V epoxide with a thiol of formula VI in the presence of a second base and an aprotic solvent, preferably in a temperature range from about −78° C. to 155° C., to form a sulfide of formula VII; and reacting the formula VII sulfide with an oxidizing agent in the presence of an aprotic solvent, preferably in a temperature range from about −78° C. to 155° C.

Aprotic solvents suitable for use in this invention include, but are not limited to, halogenated hydrocarbons such as dichloromethane, carbon tetrachloride, chloroform, 1,2-dichloroethane, and the like; hydrocarbons such as hexane, heptane, and the like; aromatic hydrocarbons such as benzene, toluene, a xylene, mesitylene, and the like; halogenated aromatic hydrocarbons such as fluorobenzene, chlorobenzene, bromobenzene, a dihalobenzene, and the like; an ether such as diethyl ether, methyl t-butyl ether, tetrahydrofuran, and the like; an ester such as ethyl acetate, and the like; and an amide such as N,N-dimethylformamide, and the like; and mixtures thereof. In a preferred embodiment of the present invention, step (a) is conducted in the presence of an amide, preferably N,N-dimethylformamide; step (b) is conducted in the presence of a halogenated hydrocarbon, preferably dichloromethane; step (c) is conducted in the presence of an ether, preferably tetrahydrofuran; and step (d) is conducted in the presence of a halogenated hydrocarbon, preferably dichloromethane.

First and second bases useful in the processes of this invention include, but are not limited to, alkali metal hydrides such as sodium hydride, potassium hydride, and lithium hydride; alkali metal alkoxides such as sodium methoxide, potassium methoxide, sodium ethoxide, potassium ethoxide, sodium t-butoxide, potassium t-butoxide, and the like; alkali metal amides such as sodium amide, and the like; and alkyllithiums such as butyllithium, and the like. Preferred first and second bases include sodium hydride, potassium t-butoxide, sodium amide, and butyllithium with sodium hydride being more preferred.

Epoxidizing agents suitable for use in the present invention include conventional epoxidizing agents known in the art. Conventional epoxidizing agents particularly useful in the processes of this invention include, but are not limited to, peracids such as peracetic acid, trifluoroperacetic acid, 3-chloroperbenzoic acid, and the like; and dioxiranes such as dimethyldioxirane, methyltrifluoromethyldioxirane, and the like. Preferred epoxidizing agents include peracids with trifluoroperacetic acid being more preferred.

Oxidizing agents suitable for use in the oxidation of the formula VII sulfides of this invention include conventional oxidizing agents known in the art. Conventional oxidizing agents particularly useful for the oxidation of the formula VII sulfide of the present invention include, but are not limited to, peracids such as peracetic acid, trifluoroperacetic acid, 3-chloroperbenzoic acid, and the like; dioxiranes such as dimethyldioxirane, methyltrifluoromethyldioxirane, and the like; hydrogen peroxide; sodium periodate; N-methylmorpholine N-oxide; and oxone. Preferred oxidizing agents include peracids with trifluoroperacetic acid being more preferred.

The peracids utilized in the epoxidation and oxidation steps of the present invention may be conveniently prepared in situ from hydrogen peroxide and the corresponding acid anhydride. For example, trifluoroperacetic acid is preferably formed in situ from hydrogen peroxide and trifluoroacetic anhydride.

In a preferred process of the present invention, $R_3$ is trifluoromethyl. In another preferred process of this invention, X is F, Cl, Br or I, more preferably F.

Preferred formula I compounds produced by the process of the present invention are those wherein
Y is cyano, nitro or trifluoromethyl;
R is trifluoromethyl, cyano, nitro, methoxy or methyl;
$R_1$ is methyl or trifluoromethyl; and
$R_2$ is alkyl,
  phenyl optionally substituted with one fluoro, chloro, cyano, nitro, methoxy or methylthio substituent, or
  thienyl, imidazolyl, thiazolyl, benzothiazolyl, thiadiazolyl, pyridyl or pyrimidinyl each optionally substituted with one chloro, bromo or methyl substituent.

More preferred formula I compounds prepared by the process of this invention are those wherein
Y is cyano or nitro;
R is trifluoromethyl;
$R_1$ is methyl; and
$R_2$ is $C_1$–$C_4$alkyl, phenyl, p-fluorophenyl, thiazol-2-yl, 4-methylthiazol-2-yl, 5-methyl-1,3,4-thiadiazol-2-yl or 2-pyridyl.

The process of the present invention is particularly useful for the preparation of bicalutamide.

Optical isomers of the formula I compounds may be obtained by conducting the step (b) epoxidation under asymmetric conditions to give chiral compounds. For example, the formula IV propanamide may be epoxidized with a chiral dioxirane to give a chiral epoxide.

Listed below are definitions of various terms used herein. These definitions apply to the terms as they are used throughout the specification (unless they are otherwise limited in specific instances) either individually or as part of a larger group.

It should be noted that any heteroatom with unsatisfied valences is assumed to have the hydrogen atoms necessary to satisfy the valences.

The term "alkyl" or "alk" refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, $R_4$ as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include, but are not limited to, one or more of the following groups: halo (such as F, Cl, Br or I), haloalkyl (such as $CCl_3$ or $CF_3$), alkoxy, alkylthio, hydroxy, carboxy (—COOH), alkoxycarbonyl, alkylcarbonyloxy, amino (—$NH_2$), carbamoyl, urea, amidinyl or thiol (—SH).

The terms "alkoxy" or "alkylthio", as used herein, denote an alkyl group as described above bonded through an oxygen linkage (—O—) or a sulfur linkage (—S—), respectively.

Sulfonyl denotes groups bonded by —$SO_2$-linkages.

The term "alkoxycarbonyl", as used herein, denotes an alkoxy group bonded through a carbonyl group.

The term "alkylcarbonyl" refers to an alkyl group bonded through a carbonyl group.

The term "aryl" refers to monocyclic or bicyclic aromatic rings, e.g., phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to, halogen, alkyl, alkoxy, hydroxy, carboxy, carbamoyl, alkoxycarbonyl, nitro, trifluoromethyl, amino, cyano, alkyl $S(O)_t$ (t=0, 1 or 2) or thiol.

The term "heteroaryl" refers to a monocyclic aromatic hydrocarbon group having 5 or 6 ring atoms, or a bicyclic aromatic group having 8 to 10 atoms, containing at least one heteroatom, O, S, or N, in which a carbon or nitrogen atom is the point of attachment, and in which one or two additional carbon atoms is optionally replaced by a heteroatom selected from O or S, and in which 1 to 3 additional carbon atoms are optionally replaced by nitrogen heteroatoms, said heteroaryl group being optionally substituted as described herein. Exemplary heteroaryl groups include the following: thienyl, furyl, pyrrolyl, pyridyl, imidazolyl, thiadiazolyl, thiazolyl, oxazolyl, triazolyl, pyrazolyl, isoxazolyl, isothiazolyl, pyrazinyl, tetrazolyl, pyridazinyl, pyrimidinyl, triazinylazepinyl, indolyl, isoindolyl, quinolinyl, isoquinolinyl, benzothiazolyl, benzoxazolyl, benzimidazolyl, benzoxadiazolyl and benzofurazanyl. Exemplary substituents include one or more of the following: halogen, alkyl, alkoxy, hydroxy, carboxy, carbamoyl, alkoxycarbonyl, trifluoromethyl, nitro, cyano, amino, alkylS $(O)_t$(t=0, 1 or 2) or thiol.

The term "halogen" or "halo" refers to chlorine, bromine, fluorine or iodine.

The term "perfluoroalkyl" refers to a $C_nF_2n+1$ group wherein n is an integer of 1 to 6.

Starting compounds of formulas II and III are known to those skilled in the art. Those starting compounds may be prepared by procedures known in the art or are commercially available.

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of N-[4-Cyano-3-(trifluoromethyl) phenyl]methacrylamide

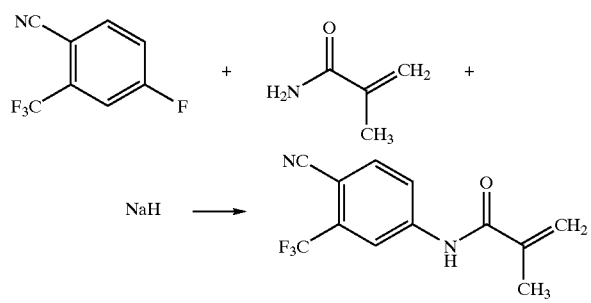

To a solution of methacrylamide (153.00 g, 1797.88 mmol) in 800 mL of N,N-dimethylformamide was added 4-cyano-3-(trifluoromethyl)phenyl fluoride (200 g, 1057.58 mmol) at room temperature. The solution was cooled in a methanol/dry ice bath to −20° C. To this cooled solution was added sodium hydride (102 g, 2696.84 mmol), portion-wise, while keeping the reaction mixture temperature below 70° C. The reaction mixture was allowed to cool to room temperature and stirred for 4 hours under nitrogen atmosphere. Water (915 mL) was added followed by 18% HCl (250 mL) and hexane (970 mL). The resultant slurry was allowed to stir overnight. The solid was filtered, washed sequentially with water (3×150 mL) and hexane (100 mL), and dried at 60° C. to give the title product as an off white solid (260 g, 97%).

$^1$H NMR (CDCl$_3$) δ 7.87 (d, J=1.9 Hz, 1H), 7.80 (dd, J=1.9, 8.5 Hz, 1H), 7.69 (bs, 1H), 7.62 (d, J=8.5 Hz, 1H), 5.69 (s, 1H), 5.44 (t, J=1.5 Hz, 1H), 1.90 (s, 3H).

EXAMPLE 2

Preparation of N-[4-Cyano-3-(trifluoromethyl) phenyl]methacrylamide epoxide

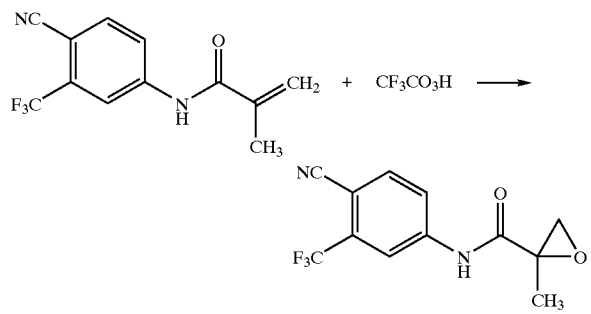

Preparation 1

To a stirred solution of N-[4-cyano-3-(trifluoromethyl) phenyl]meth-acrylamide (250 g, 983.4 mmol) in dichloromethane (1.2 L) was added 30% hydrogen peroxide (170 mL, 5900.6 mmol). The solution was cooled in a methanol/ dry ice bath to −60° C. Trifluoroacetic anhydride (791.76 mL, 5605.6 mmol) was added slowly while keeping the reaction mixture temperature between −15 to 0° C. After the addition was complete, the reaction mixture was stirred at room temperature for 45 minutes under a nitrogen atmosphere, transferred to a separation funnel and diluted with water (1 L). The organic layer was collected, and the aqueous layer was extracted with dichloromethane (3×200 mL). The organic layers were combined, washed sequentially with saturated sodium bisulfite (1 L) and water (1 L), dried over sodium sulfate, and distilled. The residue was diluted with ethyl acetate (160 mL) and tert-butyl methyl ether (1.6 L). The resultant slurry was stirred overnight, filtered and dried at 60° C. to give the title product as a white solid (180 g, 68%). $^1$H NMR (CDCl$_3$) δ 8.54 (s, 1H), 8.16 (d, J=1.9 Hz, 1H), 8.05 (dd, J=1.9, 8.5 Hz, 1H), 7.95 (d, J=8.5 Hz, 1H), 3.16 (s, 2H), 1.83 (s, 3H).

Preparation 2

To a stirred solution of N-[4-cyano-3-trifluoromethyl) phenyl]methacrylamide (1.8 g, 7.08 mmol), and dichloromethane (10 mL) was added hydrogen peroxide (1.22 mL, 42.5 mmol). The flask was then put in a water bath at room temperature. Trifluoroacetic anhydride (5 mL, 35.40 mmol) was added slowly. The reaction mixture was stirred and checked by HPLC. After 1 h and 40 minutes, the reaction mixture was transferred to a separation funnel using dichloromethane (35 mL). The organic layer was then washed with distilled water (15 mL), saturated aqueous sodium bisulfite (4×15 mL), saturated sodium bicarbonate (3×15 mL), brine (15 mL), dried over magnesium sulfate, filtered, concentrated and dried to give the title compound as a yellowish solid (1.94 g, 98.6% yield).

EXAMPLE 3

Preparation of N-[4-Cyano-3-(trifluoromethyl) phenyl]-3-[(4-fluorophenyl)thio]-2-hydroxy-2-methylpropanamide

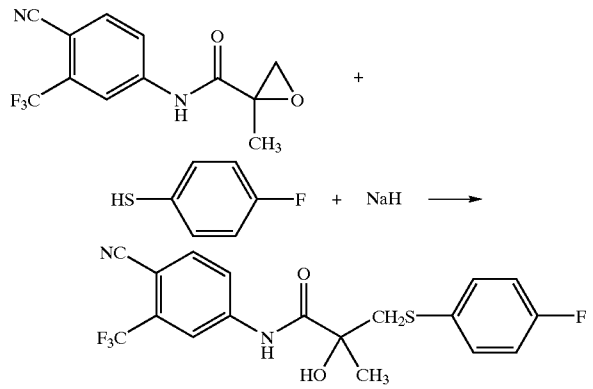

To a 0° C. mixture of sodium hydride (19.3 g, 804.8 mmol) in tetrahydrofuran (333 mL) was added a solution of 4-fluorobenzenethiol (81.8 mL, 767.92 mmol) in tetrahydrofuran (248 mL) while maintaining the temperature below 25° C. during the addition. After the addition was complete, the mixture was stirred for five minutes, and a solution of N-[4-cyano-3-(trifluoromethyl)phenyl]methacryalmide epoxide (166 g, 614.3 mmol) in tetrahydrofuran (830 mL) was added slowly. The reaction mixture was stirred at room temperature for two hours, and the solvent was distilled off. The residue was diluted with ethyl acetate (885 mL), transferred to a separation funnel and washed sequentially with brine (220 mL) and water (440 mL). The organic layer was dried with magnesium sulfate, filtered, and concentrated to give the title product as a clear oil which solidified on standing (244.74 g, 100%). $^1$H NMR (CDCl$_3$) δ 9.05 (s, 1H), 7.88 (m, 2H), 7.69 (m, 2H), 7.30 (m, 2H), 6.78 (d, J=1.3 Hz, 1H), 3.77 (br, 1H), 3.63 (d, J=14.0 Hz, 1H), 3.03 (d, J=14.0 Hz, 1H), 1.46 (s, 3H).

EXAMPLE 4

Preparation of N-[4-Cyano-3-(trifluoromethyl) phenyl]-3-[4-fluorophenyl)sulfonyl]-2-hydroxy-2-methylpropanamide (bicalutamide)

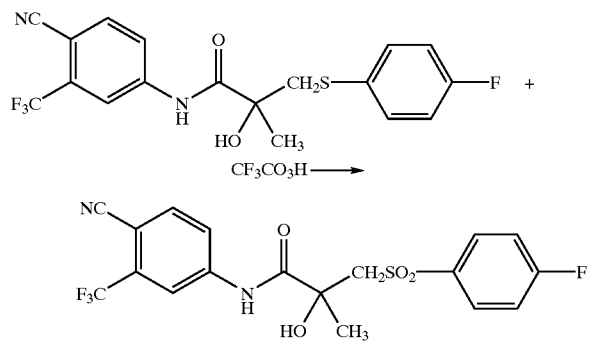

To a solution of N-[4-cyano-3-(trifluoromethyl)phenyl]-3-[(4-fluorophenyl)thio]-2-hydroxy-2-methylpropanamide (244.74 g, 614.3 mmol) in dichloromethane (1.5 L) was added 30% hydrogen peroxide (141.6 mL, 4914.7 mmol). The mixture was cooled to −55° C. Trifluoroacetic anhydride (520.6 mL, 3686.0 mmol) was added slowly while keeping the reaction mixture temperature between −15 to 0° C. After the addition was complete, the reaction mixture was stirred at room temperature for 16 hours, and diluted with ice cold water (500 mL) and brine (500 mL). The resultant slurry was stirred for 20 minutes, filtered, washed with tert-butyl methyl ether, and dried to give the title product as a white solid (255.2 g, 97%).

$^1$H NMR (DMSO-d$_6$) δ 10.40 (s, 1H), 8.44 (s, 1H), 8.22 (d, J=8.6 Hz, 1H), 8.10 (d, J=8.6 Hz, 1H), 7.93 (m, 2H), 7.38 (t, J=8.4 Hz, 2H), 6.42 (s, 1H), 3.95 (d, J=14.7 Hz, 1H), 3.72 (d, J=14.7 Hz, 1H), 1.40 (s, 3H).

What is claimed is:

1. A process for the preparation of an N-(substituted phenyl)-3-alkyl-, aryl- or heteroarylsulfonyl-2-hydroxy-2-alkyl- or haloalkylpropanamide of formula I

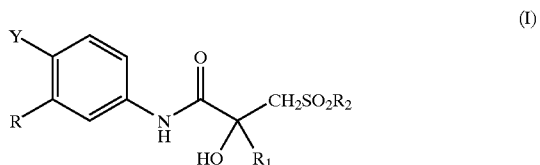

(I)

wherein

Y is cyano, nitro, perfluoroalkyl, alkylcarbonyl, alkoxycarbonyl or alkylsulfonyl;

R is perfluoroalkyl, cyano, nitro, alkylcarbonyl, alkoxycarbonyl, alkyl or alkoxy;

$R_1$ is alkyl or haloalkyl; and $R_2$ is alkyl, aryl or heteroaryl, which process comprises:

(a) reacting a substituted benzene of formula II (II)

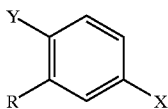

wherein Y and R are as described above, X is F, Cl, Br, I or $-OSO_2R_3$, and $R_3$ is alkyl or aryl with an α,β-unsaturated propanamide of formula III

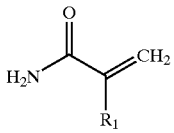

wherein $R_1$ is as described above in the presence of a first base to form an N-(substituted phenyl)-α,β-unsaturated propanamide of formula IV

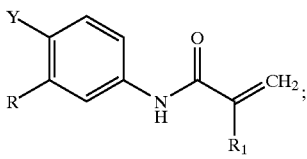

(b) reacting the formula IV propanamide with an epoxidizing agent to form an epoxide of formula V

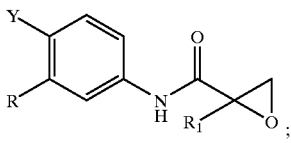

(c) reacting the formula V epoxide with a thiol of formula VI

 (VI)

wherein $R_2$ is as described above in the presence of a second base to form a sulfide of formula VII

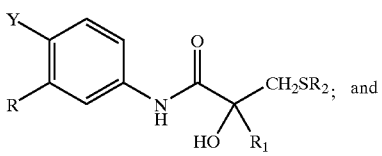

(d) reacting the formula VII sulfide with an oxidizing agent.

2. The process according to claim 1 wherein the first and second bases are independently selected from the group consisting of an alkali metal hydride, an alkali metal alkoxide, an alkali metal amide and an alkyllithium.

3. The process according to claim 1 wherein the first and second bases are independently selected from the group consisting of sodium hydride, potassium t-butoxide, sodium amide and butyllithium.

4. The process according to claim 1 wherein the first and second bases are sodium hydride.

5. The process according to claim 1 wherein the epoxidizing agent is selected from the group consisting of a peracid and a dioxirane.

6. The process according to claim 1 wherein the epoxidizing agent is selected from the group consisting of peracetic acid, trifluoroperacetic acid and 3-chloroperbenzoic acid.

7. The process according to claim 1 wherein the epoxidizing agent is trifluoroperacetic acid.

8. The process according to claim 7 wherein the trifluoroperacetic acid is formed in situ from hydrogen peroxide and trifluoroacetic anhydride.

9. The process according to claim 1 wherein the oxidizing agent is selected from the group consisting of a peracid, a dioxirane, hydrogen peroxide, sodium periodate, N-methylmorpholine N-oxide and oxone.

10. The process according to claim 1 wherein the oxidizing agent is a peracid.

11. The process according to claim 10 wherein the peracid is selected from the group consisting of peracetic acid, trifluoroperacetic acid and 3-chloroperbenzoic acid.

12. The process according to claim 1 wherein the oxidizing agent is trifluoroperacetic acid.

13. The process according to claim 12 wherein the trifluoroperacetic acid is formed in situ from hydrogen peroxide and trifluoroacetic anhydride.

14. The process according to claim 1 wherein steps (a)–(d) are conducted in the presence of an aprotic solvent.

15. The process according to claim 14 wherein the aprotic solvent is selected from the group consisting of a halogenated hydrocarbon, a hydrocarbon, an aromatic hydrocarbon, a halogenated aromatic hydrocarbon, an ether, an ester and an amide and mixtures thereof.

16. The process according to claim 1 wherein step (a) is conducted in the presence of N,N-dimethylformamide, step (b) is conducted in the presence of dichloromethane, step (c) is conducted in the presence of tetrahydrofuran, and step (d) is conducted in the presence of dichloromethane.

17. The process according to claim 1 wherein $R_3$ is trifluoromethyl.

18. The process according to claim 1 wherein
Y is cyano, nitro or trifluoromethyl;
R is trifluoromethyl, cyano, nitro, methoxy or methyl;
$R_1$ is methyl or trifluoromethyl; and
$R_2$ is alkyl,
phenyl optionally substituted with one fluoro, chloro, cyano, nitro, methoxy or methylthio substituent, or
thienyl, imidazolyl, thiazolyl, benzothiazolyl, thiadiazolyl, pyridyl or pyrimidinyl each optionally substituted with one chloro, bromo or methyl substituent.

19. The process according to claim 1 wherein
Y is cyano or nitro;
R is trifluoromethyl;
$R_1$ is methyl; and
$R_2$ is $C_1$–$C_4$alkyl, phenyl, p-fluorophenyl, thiazol-2-yl, 4-methylthiazol-2-yl, 5-methyl-1,3,4-thiadiazol-2-yl or 2-pyridyl.

20. The process according to claim 1 for the preparation of
N-[4-cyano-3-(trifluoromethyl)phenyl]-3-[(4-fluorophenyl)sulfonyl]-2-hydroxy-2-methylpropanamide.

21. A process for the preparation of an N-(substituted phenyl)-α,β-unsaturated propanamide of formula IV

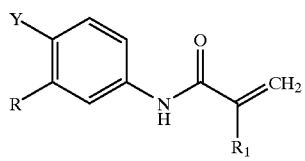

wherein

Y is cyano, nitro, perfluoroalkyl, alkylcarbonyl, alkoxycarbonyl or alkylsulfonyl;

R is perfluoroalkyl, cyano, nitro, alkylcarbonyl, alkoxycarbonyl, alkyl or alkoxy; and $R_1$ is alkyl or haloalkyl, which process comprises reacting a substituted benzene of formula II

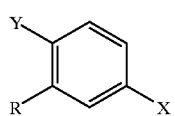

wherein Y and R are as described above, X is F, Cl, Br, I or $-OSO_2R_3$, and $R_3$ is alkyl or aryl with an α,β-unsaturated propanamide of formula III

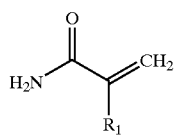

wherein $R_1$ is as described above in the presence of a base.

22. A process for the preparation of an epoxide of formula V

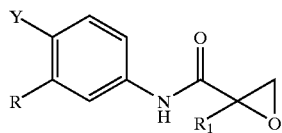

wherein

Y is cyano, nitro, perfluoroalkyl, alkylcarbonyl, alkoxycarbonyl or alkylsulfonyl;

R is perfluoroalkyl, cyano, nitro, alkylcarbonyl, alkoxycarbonyl, alkyl or alkoxy; and $R_1$ is alkyl or haloalkyl, which process comprises:

(a) reacting a substituted benzene of formula II (II)

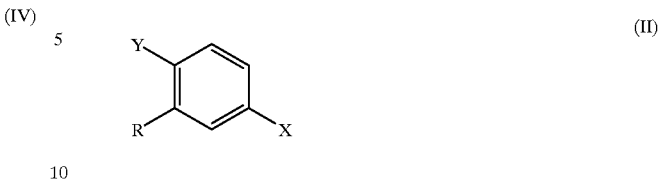

wherein Y and R are as described above, X is F, Cl, Br, I or $-OSO_2R_3$, and $R_3$ is alkyl or aryl with an α,β-unsaturated propanamide of formula III

wherein $R_1$ is as described above in the presence of a base to form an N-(substituted phenyl)-α,β-unsaturated propanamide of formula IV

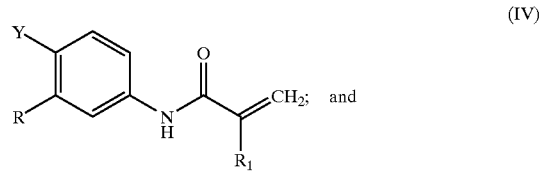

(b) reacting the formula IV propanamide with an epoxidizing agent.

23. A process for the preparation of a sulfide of formula VII

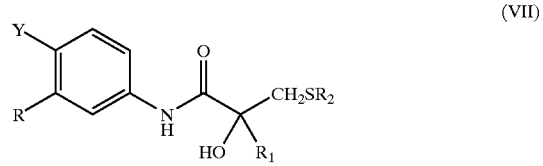

wherein

Y is cyano, nitro, perfluoroalkyl, alkylcarbonyl, alkoxycarbonyl or alkylsulfonyl;

R is perfluoroalkyl, cyano, nitro, alkylcarbonyl, alkoxycarbonyl, alkyl or alkoxy;

$R_1$ is alkyl or haloalkyl; and $R_2$ is alkyl, aryl or heteroaryl, which process comprises:

(a) reacting a substituted benzene of formula II

wherein Y and R are as described above, X is F, Cl, Br, I or —OSO$_2$R$_3$, and R$_3$ is alkyl or aryl with an α,β-unsaturated propanamide of formula III

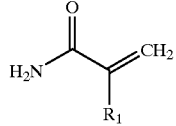
(III)

wherein R$_1$ is as described above in the presence of a first base to form an N-(substituted phenyl)-α,β-unsaturated propanamide of formula IV

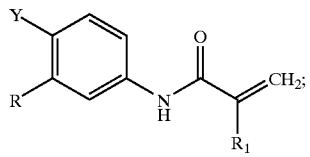
(IV)

(b) reacting the formula IV propanamide with an epoxidizing agent to form an epoxide of formula V (V)

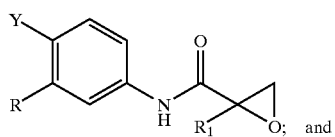
(V)

(c) reacting the formula V epoxide with a thiol of formula VI

R$_2$SH  (VI)

wherein R$_2$ is as described above in the presence of a second base.

* * * * *